(12) United States Patent
Kekalainen et al.

(10) Patent No.: US 9,927,278 B2
(45) Date of Patent: Mar. 27, 2018

(54) SENSOR DEVICE FOR SMART WASTE COLLECTION SYSTEMS AND METHOD

(71) Applicant: Enevo Oy, Espoo (FI)

(72) Inventors: Fredrik Kekalainen, Espoo (FI); Johan Engstrom, Tuusula (FI)

(73) Assignee: Enevo Oy, Espoo (FI)

( * ) Notice: Subject to any disclaimer, the term of this patent is extended or adjusted under 35 U.S.C. 154(b) by 316 days.

(21) Appl. No.: 14/761,404

(22) PCT Filed: Jan. 28, 2014

(86) PCT No.: PCT/EP2014/000223
§ 371 (c)(1),
(2) Date: Jul. 16, 2015

(87) PCT Pub. No.: WO2014/114469
PCT Pub. Date: Jul. 31, 2014

(65) Prior Publication Data
US 2015/0323366 A1    Nov. 12, 2015

(51) Int. Cl.
*G06F 11/00* (2006.01)
*G01F 17/00* (2006.01)
(Continued)

(52) U.S. Cl.
CPC ............ *G01F 17/00* (2013.01); *G01D 11/30* (2013.01); *G01N 25/00* (2013.01); *G01N 25/56* (2013.01);
(Continued)

(58) Field of Classification Search
None
See application file for complete search history.

(56) References Cited

U.S. PATENT DOCUMENTS

| 4,282,591 A | 8/1981 | Andreuccetti |
| 2003/0038415 A1 | 2/2003 | Anderson et al. |
| 2004/0098068 A1* | 5/2004 | Carbunaru ........... A61N 1/3605 607/60 |

FOREIGN PATENT DOCUMENTS

| CN | 101642779 A | 2/2010 |
| DE | 4334509 A1 | 4/1995 |

(Continued)

OTHER PUBLICATIONS

Englsih Translation of FR2952714A1, pp. 1-4.*
(Continued)

*Primary Examiner* — Shaun Campbell
(74) *Attorney, Agent, or Firm* — Ziegler IP Law Group, LLC

(57) ABSTRACT

A sensor device for remote monitoring of a waste container, the sensor device including one or more sensors for sensing an amount of waste and an environment within the waste container, a data processing unit for processing sensor signals indicative of the amount of waste and the environment within the waste container, a communication interface for enabling the sensor device to communicate information corresponding to the sensor signals to a remote location. The sensor device is mounted to an upper lid of the waste container in a spaced apart manner by placing one or more spacing elements and a heat reflecting layer arranged between the sensor device and the upper lid to provide a thermal barrier between an underside surface of the waste container lid and the sensor device.

20 Claims, 11 Drawing Sheets

(51) Int. Cl.
*G01N 25/00* (2006.01)
*G01N 25/56* (2006.01)
*G01N 29/04* (2006.01)
*G01N 33/00* (2006.01)
*G01D 11/30* (2006.01)

(52) U.S. Cl.
CPC ......... *G01N 29/04* (2013.01); *G01N 33/0009* (2013.01)

(56) References Cited

FOREIGN PATENT DOCUMENTS

| | | |
|---|---|---|
| DE | 202 10 495 U1 | 11/2003 |
| DE | 20210495 U1 | 11/2003 |
| ES | 2281215 A1 | 9/2007 |
| FR | 28552 A1 | 11/2004 |
| FR | 2952714 A1 * 5/2011 ............ B65F 1/1447 |
| WO | 2011/058287 A1 | 5/2011 |
| WO | 2012/015664 A1 | 2/2012 |

OTHER PUBLICATIONS

International Search Report; PCT/EP2014/000223; dated Sep. 3, 2014; 7 Pages.
Combined Search and Examination Report received for United Kingdom Patent Application No. GB1301501.1, dated Jun. 6, 2013, 7 pages.
Examination Report received for United Kingdom Patent Application No. GB1301501.1, dated Feb. 28, 2014, 3 pages.
International Search Report received for International Patent Application No. PCT/EP2014/000223, dated Sep. 3, 2014, 6 pages.

* cited by examiner

SENSOR DEVICE FOR SMART WASTE COLLECTION SYSTEMS AND METHOD

FIELD OF THE DISCLOSED EMBODIMENTS

The aspects of the disclosed embodiments relate to sensor systems comprising sensor devices for use when implementing smart waste collection systems, for example to sensor devices for smart waste collection systems, wherein the systems include one or more smart trash containers including one or more associated sensor devices, and wherein the one or more sensor devices are wireless-enabled for communicating to a control centre for receiving waste-indicative signals from the one or more smart trash containers for devising an optimal schedule for one or more waste collection vehicles to collect waste from the one or more smart trash containers. Moreover, the aspects of the disclosed embodiments concern methods of installing aforesaid sensor devices to trash containers to convert them to smart trash containers.

BACKGROUND

As human population grows, as human population's standard of living improves resulting in more use of Earth's resources, and Earth's resources become increasing depleted with progression of time, there arises an increased need to recycle materials and reduce generation of waste. Moreover, there is also an increasing need to ensure that such recycling is executed in a manner which itself employs as few resources as possible, namely in manner which is most efficient.

In technologically-advanced countries, waste management industries are growing in importance and need to employ increasingly efficient processes to increase revenue margins, namely such waste management industries need to optimize their resource utilization, for example use of waste collection vehicles, use of waste collection personnel and similar. Based upon contemporary data from Environmental Business International, the United States of America (USA) has a solid-waste management industry which has grown in value from 39.4 billion US dollars in the year 2000 to 52.40 billion US dollars in the year 2010.

An effective manner to increase operating efficiency in waste management industries is to implement waste containers, namely "trash containers", in a smart manner. Such a smart manner requires one or more sensor devices to be attached to each waste container, wherein the one or more sensor devices are wireless-enabled for communicating to a waste-collection coordinating arrangement, for example a waste-collection control centre, and one or more sensors for sensing a quantity and/or state of waste in the container. Moreover, there is also a need to be able to retrofit such one or more sensor devices to existing waste containers to convert them to being smart waste containers.

Several problems are encountered in practice when implementing an aforementioned waste management system employing a plurality of smart waste containers which are spatially distributed at customer premises. A first problem arising is that the waste containers themselves are often housed outside buildings and hence subject to extremes of weather conditions, for example sub-zero temperatures in winter, and elevated temperatures in summer due to incident solar radiation thereupon; in consequence, their sensor devices need to be able to function over a wide range of environmental temperatures. A second problem is that waste containers often need to be substantially sealed when in a closed state, for example to prevent animals such as rats, mice and insects gaining access to contents of the waste containers that could result in a public health risk; when wet waste is placed into the waste containers, a humidity within the waste containers is potentially high, with a risk of condensation occurring on an inside lid surface and walls of the waste containers, for example when a sudden fall in external temperature outside the waste containers occurs, for example at dusk after a warm summer day. A third problem encountered is that contemporary waste containers are often fabricated from molded plastics materials which are effective thermal insulators, such that internal volumes of the waste containers, especially lid regions thereof, can potentially become very high when the waste containers are exposed to strong sunlight having an energy density of circa 500 W/m$^2$ to 1000 W/m$^2$. A fourth problem encountered is that it is highly desirable that the sensor devices be retrofitted to existing waste containers to render them as smart containers at their locations of deployment, namely installed in situ, thereby avoiding a need to transport the waste containers to a fitting centre to have their sensor devices fitted, and then transport the waste containers back to their respective deployment locations again; beneficially, fitting of the sensor devices is executable by a single member of personnel, even when large waste containers having lids with areas in excess of 1 m$^2$ are to be retrofitted with one or more sensor devices.

Known sensor devices for implementing smart waste containers are not able to address the aforementioned problems in a satisfactory manner.

In a published Japanese patent publication no. JP09144712A (Koganei Corp.), there is described a mounting structure for a sensor switch. The mounting structure includes a sensor holder which is fixed to a mounted member by employing a screw. Moreover, the sensor switch is installed into the sensor holder by pressing it against the sensor holder, wherein the sensor holder flexes to receive the sensor switch in a secure manner. Although such a mounting structure is suitable for installation of a sensor switch, it is unsuitable for use with the one or more aforementioned one or more sensor devices required for implementing a smart waste container. Document WO 2012/015664 presents a waste enclosure device comprising a waste enclosure employing operational functions including collection and monitoring capacity wherein said device includes one or more programmable logic controllers. Operational functions are performed by electrical components including sensors to determine waste deposits characteristics and contents. Said device operational functions are further adapted to send and receive data, optionally wirelessly, and configured and adapted to utilize solar derived electric power and, optionally, electric power from other sources. Document WO 2011/058287 discloses a device for measuring a filling rate of a container comprising: an attachment means suitable for attaching the device to an inner surface of the container; a sensor suitable for measuring said filling rate and generating data; an electronic module comprising a clock and a telecommunication means and being suitable for triggering the sensor, receiving and sending the data to a remote apparatus; and a source suitable for supplying electric power to the electronic module and the sensor. Document DE 20210495 shows a plastic molded wheeled waste bin having a flexible electrical resistance sensor which conveys a value to a transmitter unit on the outside of the rear wall which inductively communicates with a receiver unit on the collection vehicle to indicate the capacity of the contents. Document U.S. Pat. No. 4,282,591 discusses a light control and indicating device including a main component adapted for mounting in a cavity of a wall, and a cover plate fitted there over. The main component includes a frame or holder on which are mounted a plurality of operating members (referred to below) and those members have indicating elements exposed through, or slightly projecting through, openings in the cover plate. Document US 2003/038415 presents a sensor isolation system including a sensor, a package for the sensor, and a compliant interposer disposed between the sensor and the package and interconnecting the sensor to the package to isolate the sensor from thermal and mechanical stresses and yet at the same time providing a physical interconnect between the sensor and the package.

SUMMARY

The aspects of the disclosed embodiments seek to provide a sensor system comprising a sensor device for implementing in monitoring a waste container, wherein the sensor device addresses aforementioned problems of installation and during the operation of the sensor device in a hostile environment presented by a waste container when deployed.

According to a first aspect of the disclosed embodiments, there is provided a sensor system comprising a sensor device implemented in monitoring a waste container in real time and remotely: there is provided a sensor system comprising a sensor device for implementing a smart waste container, characterized in that the sensor system comprises one or more spacing elements, a heat reflecting layer and a mounting arrangement for mounting the sensor device to an upper portion of the smart waste container, wherein the mounting arrangement is arranged to provide a thermal barrier between a majority of an area of the sensor device facing towards the upper portion of the smart waste container to which the sensor device is mounted when in operation.

The disclosed embodiments are of advantage in that the thermal barrier assists the sensor device to operate in hostile environmental conditions encountered in operation at the upper portion of the waste container.

Optionally, the sensor device is implemented such that the thermal barrier includes an air gap between a majority of the area of the sensor device and the upper portion of the smart waste container. More optionally, the thermal barrier has a height in a range of 1 mm to 20 mm, when the sensor device is mounted in operation to the upper portion of the smart waste container. More optionally, the thermal barrier has a height in a range of 2 mm to 10 mm, when the sensor device is mounted in operation to the upper portion of the smart waste container.

Optionally, the sensor device is implemented such that the thermal barrier includes reflective metal foil for reflecting thermal radiation from the upper portion of the smart waste container back towards the upper portion.

Optionally, the sensor device is arranged to be attachable to a lid of the waste container.

Optionally, the sensor device includes one or more sensors for sensing an amount of waste and/or and an environment within the waste container, a data processing unit for processing sensor signals generated by the one or more sensors indicative of the amount of waste in the container and/or the environment within the container, and a communication interface coupled to the data processing arrangement for enabling the sensor device to communicate information corresponding to the sensor signals to a location which is spatial remote relative to the sensor device. More optionally, the one or more sensors include one or more of:

(a) a sensor for determining the quantity of waste present within the waste container;
(b) a temperature sensor for measuring a temperature within the waste container;
(c) a gas sensor for monitoring atmospheric conditions within the waste container; and
(d) a humidity sensor for measuring humidity within the waste container.

Optionally, the sensor device is implemented such that the heat reflective layer arranged between the sensor device and the upper lid of the waste container is a reflective metal foil to enable the sensor device to maintain a workable operating temperature.

Optionally, the sensor device is implemented such that the one or more spacing elements in combination with an air gap is adapted to maintain the sensor device at an acceptable temperature during operation.

Optionally, in the sensor device, the sensor for determining the quantity of waste present within the waste container is implemented by way of an ultrasonic sensor arrangement. More optionally, the ultrasonic arrangement is included within a housing of the sensor device and has a port, whereat ultrasonic radiation is emitted and received, disposed inside an outwardly-tapered hole implemented through the housing through which condensation is ducted in operation.

Optionally, in the sensor device, the gas sensor for monitoring atmospheric conditions within the waste container is implemented by way of a hydrocarbon gas sensor.

Optionally, the sensor device includes one or more peripheral projections for defining the thermal barrier when the sensor device is mounted to the waste container.

Optionally, the sensor device includes a coupling arrangement for receiving a tool for use in retaining the sensor device to the waste container for enabling one or more fasteners to be installed to attach the sensor device to the waste container.

There is also provided a method of installing a sensor device pursuant to the first aspect of the disclosed embodiments, the method including:

(a) attaching a mounting tool to a housing of the sensor device;
(b) preparing a configuration of holes in the upper portion of the waste container;
(c) using the mounting tool to retain the sensor device attached thereby to the upper portion of the waste container;
(d) attaching one or more fasteners to affix the sensor device to the upper portion of the waste container via the configuration of holes; and
(e) removing the mounting tool from the housing of the sensor device.

There is further provided a tool for use in implementing the method, wherein the tool is elongate, and includes an arrangement at one end thereof for engaging onto a housing of the sensor device and one or more elements along the tool for retaining the sensor device to the upper portion of the waste container.

It will be appreciated that features of the disclosed embodiments are susceptible to being combined in various combinations without departing from the scope of the disclosed embodiments as defined by the appended claims.

DESCRIPTION OF THE DIAGRAMS

Embodiments of the disclosed embodiments will now be described, by way of example only, with reference to the following diagrams wherein.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS

Figure 1:
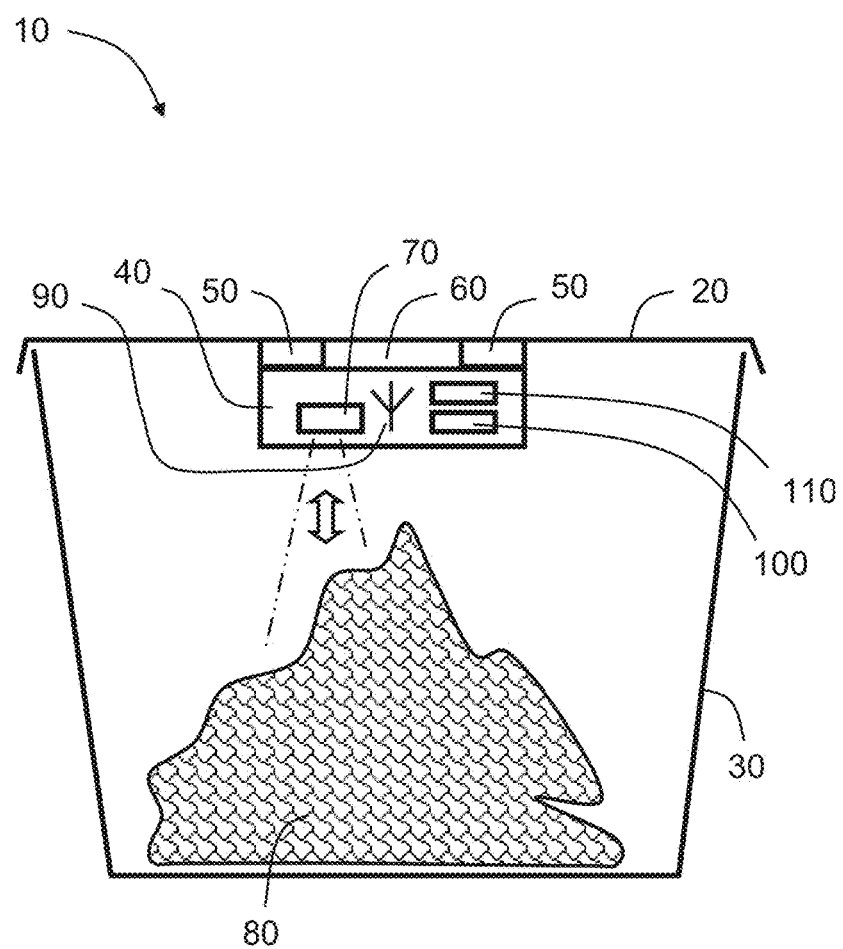
FIG. 1 is an illustration of a waste container including an embodiment of a sensor device pursuant to the disclosed embodiments installed on an underside surface of a lid of the waste container.

Referring to FIG. 1, there is shown an illustration of a smart waste container indicated generally by 10. The smart waste container 10 includes a main body 30 and a lid 20 which is optionally pivotally mounted at an upper portion of the main body 30. Optionally, the main body 30 and the lid 20 are fabricated as injection-molded components. In operation, the main body 30 is positioned on a supporting surface, for example on a concrete floor, such that the lid 20 is uppermost and exposed to incident solar radiation $S_F$ having a solar flux energy density of up to circa 1 kW/m². On an underside surface of the lid 20, facing into an interior volume of the main body 30, is mounted a sensor device 40. The sensor device 40 is mounted in a spaced-apart manner in respect to the lid 20 by way of one or more spacing elements 50, so as to provide an insulation gap, namely a "thermal barrier", for example an air gap 60, between the underside surface of the lid 20 and an external surface of the sensor device 40; optionally, the one or more spacing elements 50 are formed integrally into a housing of the sensor device 40. The sensor device 40 includes one or more sensors 70 for monitoring conditions within the interior volume of the main body 30, wherein the one or more sensors 70 include at least one of:

(a) a sensor for determining a quantity of waste 80 present within the main body 30, for example implemented by way of an ultrasonic sensor arrangement;
(b) a temperature sensor for measuring a temperature within the main body 30;
(c) a gas sensor, for example a hydrocarbon gas sensor, for monitoring atmospheric conditions within the main body 30, for example in respect of generation of methane gas within the container 10 indicative of organic waste fermentation processes occurring within the container 10; the gas sensor is beneficially implemented as a periodically-energized pellistor, a solid state gas sensor or an optical absorption gas sensor; and
(d) a humidity sensor for measuring humidity within the container 10.

The sensor device 40 additionally includes computing hardware 100 for receiving one or more sensor signals from the one or more sensors 70, and a wireless interface 90 coupled to the computing hardware 100; the sensor device 40 is thereby "wireless enabled" for wirelessly transmitting information therefrom indicative of measurements made by using the one or more sensors 70. Beneficially, the sensor device 40 is capable of enabling remote monitoring of the waste 80. The waste 80 can be any waste including but not limited to house hold waste, biodegradable waste, liquid waste, industrial waste, solid waste and similar. Optionally, the wireless interface 90 is implemented as a cellular modem, for example complying with contemporary GSM and/or 3G communication standards. The computing hardware 100 is beneficially programmed to send information corresponding to the one or more sensor signals in a constant manner, in a periodic manner, or after the one or more sensors signals exceed one or more threshold values.

In an alternative embodiment the smart waste container 10 can also be used in applications such as monitoring silos, liquid storage vessels, oil containers, coal container and other applications where the content of the container decreases and when past a lower level or threshold triggers an action such as a refilling or similar.

A significant practical problem encountered when developing and deploying early prototypes of the sensor device 40 is thermal management, as the interior volume of the container 10, for receiving the waste 80, is often not well ventilated, for example for preventing insects and similar small creatures gaining access to the waste 80. The aforesaid solar radiation absorbed by the lid 20 and the main body 30 and/or heat generated by organic decomposition processes occurring within the waste 80 can cause the lid 20 to become very hot, namely in close proximity to the sensor device 40. The sensor device 40 includes one or more batteries 110 and active electronic components which have difficulty functioning at temperatures in excess of 150° C. The one or more spacing elements 50, in combination with the air gap 60, were found to be necessary to ensure that the sensor device 40 was maintained at an acceptable temperature during operation. Beneficially, the air gap 60 has a height in a range of 1 mm to 20 mm, and more preferably a height in a range of 2 mm to 10 mm. Beneficially, an upwardly-facing surface of the sensor device 40, when the sensor device 40 is mounted to the lid 20, is provided with a reflective metal foil, for example Aluminium foil, heat-reflecting layer, to assist the sensor device 40 to maintain a workable operating temperature.

A further significant practical problem encountered with the smart waste container 10 is that, when an ambient temperature around the smart waste container 10 falls, for example at dusk, moisture inside the smart waste container 10 condenses on the underside surface of the lid 20 and also on the sensor device 40 itself. Condensed water is potentially capable of interfering with operation of electronic components included in the sensor device 40 and also with its associated one or more sensors 70, for example ultrasonic sensors which require significant excitation potentials. Moreover, as the ambient temperature further drops, for example on a cold night after the aforementioned dusk, the moisture can freeze which potentially causes further problems. An example of potential mechanical problem associated with freezing can arise if the air gap 60 is too small. If condensed water appears between the sensor device 40 and the lid 20 and happens to freeze the frozen water expands significantly causing possible fractures in the lid 10 or damage to the sensor devices 40. This can be avoided by ensuring sufficient spacing between the lid and the sensor device 40. It has been found out that if the spacing is for example below ca 1 mm the likely hood of condensed water droplets to cause mechanical problems when freezing is higher than with air gap 60 of ca 2 mm. Beneficially, the sensor device 40 is designed to cope with such environmental challenges encountered around the underside surface of the lid 20, as will be described later. Furthermore when the air gap is dimensioned to be more than ca 20 mm the likelihood that objects such as trash or other content in the container being stuck between the sensor device 40 and lid 20 increases. It is preferred that the air gap 60 is dimensioned to be larger than ca 1 mm but smaller at the range of 0.5-1.5 times and more preferably smaller than the range of 0.8-1.2, and most preferably smaller or equal to the smallest dimension of the waste in the container so that the waste does not get caught in the air gap 60. Additionally mechanical durability of the container 10 and sensor device 40 construction could be compromised if the air gap 60 or other positioned spacing element with insulating properties has a height exceeding ca 20 mm.

Further example of formation of the ice is related to relative fast temperature changes taking place around and in the waste container 10. When the outdoor temperature changes, the temperatures of the waste container (also referred to as a trash can) 10, the air inside of the waste container 10 and the sensor device 40 change in different speeds compared to each others. As an example of temperature falling from −5 degrees Celsius to −20 degrees of Celsius the waste container 10 starts to cool followed by cooling of the air inside of the waste container 10 and further followed by cooling of the sensor device 40. During the process there can be significant differences between for example the air inside of the waste container 10 and the sensor device 40. After sufficient time the temperature differences even and the waste container 10, the air inside of the trash can and the sensor device 40 will be substantially same (for example −20 Degrees Celsius). In most cases the temperature in the waste container 10 is higher than the temperature of the sensor device 40 which will result in condensation of droplets on the surface of the sensor device 40 and further to ice crystals forming on the surface. These ice crystals interfere with the performance of the sensor device 40. When temperature arises from −20 degrees to −5 degrees the waste container 10 temperature will arise first, followed by arising of the air temperature inside of the waste container 10 and finally the temperature of the sensor device 40. During warming there will be differences between the temperatures of waste container 10, air inside of the waste container 10 and the sensor device 40. Temperature differences between the air and the sensor device 40 will even up over time depending on mass and heat capacity of the sensor device 40.

When the temperature of the surface of the sensor device 40 and/or some of its components is lower than the temperature of the surrounding air (in the waste container) water vapour is likely to condensate in metallic surface of a ultrasonic sensor 300 of the sensor device 40. The water droplets form ice crystals in the surface of the ultrasonic sensor 300 and might prevent its proper operation.

Problems arising from the condensation of water and formation of crystals can be avoided if the temperature gradients between the sensor device 40 and air inside of the waste container 10 are small or non existent. In order to achieve prevent large temperature differences between the sensor device 40 and the temperature in the container 10 the thermal mass of the sensor device should be made smaller to keep total heat capacity of the sensor device 40 minimal. Small heat capacity enables sensor device 40 temperature to follow temperatures in side of the waste container 10 in a fast manner.

One exemplary way to make sensor device 40 robust and rugged is to have a moulded outer casing or so called shell of e.g. polyurethane or similar which has a high durability and is robust. Then to allow the sensor device 40 to have a small heat capacity it is preferable to have parts or all of the inner portion, which inner portion may be in one or more sections, of the casing hollow i.e. having only air (heat capacity 1.01 kJ/(kg×K)) inside of the sensor device 40 in addition to components. This might however reduce mechanical stability of the device. Based on embodiments in order to construct a mechanically stable device, which does not break easily in harsh usage environment of waste management processes, the interior of the sensor device 40 is preferably filled with a filler material to keep all components immobile in respect to top part 200 and bottom part 202 (housing) of the sensor device 40.

Table I shows two exemplary possible filler materials used inside the sensor device and their physical properties that could be used to fill the sensor device 40 to improve mechanical stability. In preferred embodiment polyurethane casing of the sensor device 40 has a filler of polyurethane based foam or similar (such as polystyrene based foam or ETA (ESD (electro sensitive devices) safe polyethylene) based foam) is used in order to have small total heat capacity of the sensor device 40. This way the sensor device 40 temperature "follows" temperature changes faster than with epoxy thus reducing formation of ice for example on top of ultrasonic sensor compared with filling the sensor device with epoxy or being solid throughout. In general the sensor device 40 should be filled with low density material while still rigid material giving mechanical stability.

Further based on test made with different configurations of the sensor device 40 it has been found out that performance of wireless interface 90 improves if the filler material has been selected as low density material such as polyurethane based foam in comparison with epoxy. Bases on test performed with the sensor device 40 it has been further found out also that selection of the filler material has impact on the energy consumption of radio communication. Preferably the filler material should be polyurethane foam due to its superior radio frequency (RF) characteristics compared to epoxy and to free air. In certain radio antenna setups it has been seen that part of the radio waves are absorbed by epoxy which has significantly higher density than polyurethane based foam.

TABLE I

Heat capacities, densities, calculated added mass (using dimensions of 130 mm diameter and 40 mm height for the sensor device 40) of the sensor device 40 when filling it with the material and needed energy for changing the temperature of the sensor with 1 degrees of Celsius.

| Material | Heat capacity (kJ/kg × K), | Density (kg/m3) | Added mass from filling material | Energy needed to change temperature of the sensor device with 1 degrees of Celsius (or Kelvin). Assuming weight of the sensor device with out added filling as 0.5 kg and heat capacity of 1 kJ/kg/K. |
|---|---|---|---|---|
| Epoxy | 1.11 | 2000 | 1 kg | 1.1 kJ + 0.5 kJ = 1.6 kJ |
| Poly-urethane foam | 1.15 | 10-60 | 0.005-0.03 kg | 0.006 kJ + 0.5 kJ = 0.506 kJ to 0.034 kJ + 0.5 kJ = 0.534 kJ |

In overview, aspects of the disclosed embodiments are concerned with mounting arrangements for a sensor device 40 for enabling it to be used in combination with waste containers 10 to provide smart waste containers which are capable of providing greater functionality for enabling more efficient waste collection and recycling to be achieved; the mounting arrangement beneficially involves providing an air gap, for example the aforementioned air gap 60, between an upper lid 20 of a waste container 10 and a sensor device 40, wherein the air gap 60 functions as a thermal insulator which reduces an impact of heat present at the lid 20 from influencing operation of the sensor device 40. Optionally, the sensor device 40 is manufactured with a reflective or white external finish, for example a white painted finish, and/or has a reflective Aluminium foil finish, for reflecting heat therefrom to maintain of the sensor device 40 at a more favourable operating temperature.

The sensor device 40 for use in the smart waste container 10, as illustrated schematically in FIG. 1, will now be described in more detail, namely in a manner which would enable a design registration to be made based upon this disclosure, for example, with reference to FIG. 2 and FIG. 10.

Figure 2:
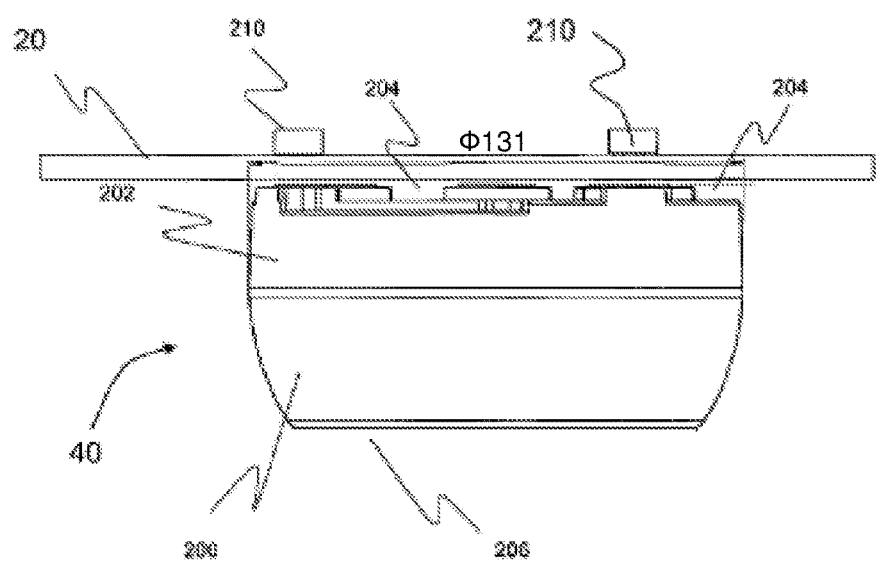
FIG. 2 is an illustration of a sensor device pursuant to the disclosed embodiments mounted to an underside surface of the lid of the waste container of FIG. 1.

Referring next to FIG. 2, the sensor device 40 is mounted in an upside-down manner onto the lid 20. The sensor device 40 includes a top part 200 and a bottom part 202 which are operable to engage mutually to one another at a grooved peripheral lip. The lower part 202 includes projections at its lower surface for forming the aforementioned spacing elements 50 for defining an air gap 204 between the bottom part 202 and the lid 20 over a majority of an lower surface area of the bottom part 202 as illustrated; beneficially, there are four projections which serve to receive mounting screws 210, wherein three of the four projections are disposed at 90° intervals, except that one of the projections is slightly angularly displaced from a 90° position as illustrated. The top part 200 is tapered, in a curved manner, with increasing distance from the lid 20. Moreover, there is also included an eccentrically-disposed hole 206 extending from the bottom part 202 to the top part 200, wherein the hole 206 has an internal wall and is included to duct condensation dripping from the lid 20 onto the bottom part 200 through the hole 206, so that the condensation is guided into the interior volume of the container 10. At a top of the top part 200, the hole 206 is provided with a peripheral lip which assists to guide condensation into the interior volume of the container 10 when the sensor device 40 is mounted upon the lid 20 when in operation. Such an implementation guides condensed water away from an ultrasonic sensor of the sensor device 40 which is employed to measure a quantity of waste 80 present within the container 10. Operating reliability of the sensor device 40 is thereby considerably improved.

The bottom part 202 and the top part 200 are beneficially manufactured to be of a generally circular form, with the top party 200 being inwardly tapered in a progressively curved manner away from the peripheral lip whereat it engages onto the bottom part 202. Moreover, the bottom part 202 and the top part 200 are beneficially injection-molded plastics material components, for example manufactured from polyurethane, ABS, Polypropylene, Polycarbonate, Polyethylene, Nylon, Urea formaldehyde resin or similar plastics material. The bottom part 202 optionally has an external diameter in a range of circa 50 mm to 200 mm, more preferably in a range of circa 10 mm to 150 mm, and more optionally a diameter of substantially 131 mm. Moreover, the sensor device 40 optionally has a height, when the bottom part 202 is assembled to the top part 200 in a range of 10 mm to 100 mm, and more optionally substantially 67 mm. The hole 206 is optionally inwardly tapered, along at least a part of its length, from the top part 200 to the bottom part 202 as illustrated, wherein the hole 206 has a widest diameter in a range of 15 mm to 75 mm, more preferably in a range of circa 25 mm to 50 mm, and more optionally a widest diameter of substantially 38 mm. The hole 206 is beneficially synergistically operable to guide ultrasonic radiation emitted and received from an ultrasonic sensor mounted along an inside wall of the hole 206, to the interior volume of the container 10 wherein the waste 80 is accommodated. The sensor device 40 is optionally used in aspects of the disclosed embodiments for miniature waste containers 10 or even smaller household bins.

Figure 3:
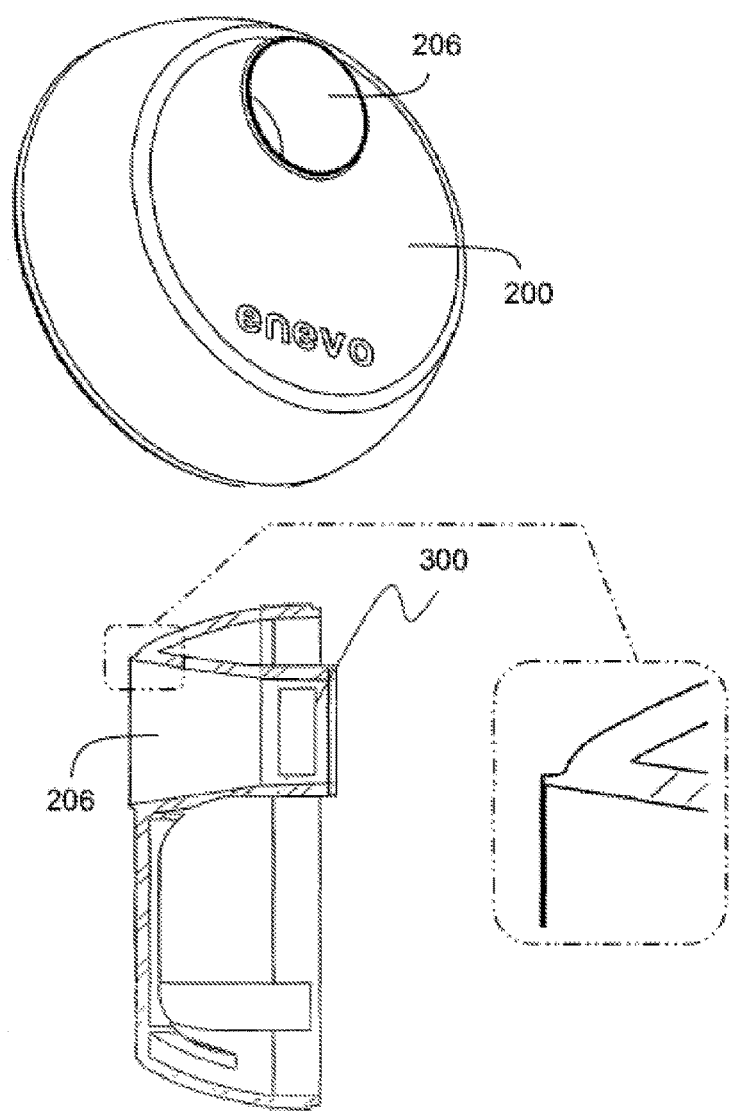
FIG. 3 is an illustration of a top part of the sensor device of FIG. 2.

Referring next to FIG. 3, the top part 200 is illustrated in greater detail, for example in a manner that also provides a basis for a design registration. In FIG. 3, a perspective view of the top part 200 is provided, with a logo "enevo" on its upper surface, and the aforesaid hole 206 in an eccentric position within the top part 200, wherein the hole 206 is inwardly tapered as aforementioned to provide an improved ultrasonic coupling between the ultrasonic sensor and the interior volume of the container 10; "enevo" is a trademark. The top part 200 is also illustrated in cross-sectional view, wherein a location of a transmitting/receiving port of the ultrasonic sensor, denoted by 300, is illustrated near a lower portion of the top part 200. The peripheral projecting edge of the hole 206 is shown in enlarged detail for guiding aforesaid condensation dripping from the lid 20. A volume adjacent to the hole 206 and within the top part 200 is designated for housing electronic components, batteries and similar functional parts; beneficially, this volume is hermetically sealed when the top part 200 and the bottom part 202 are joined together, for example by employing synthetic rubber or Silicone gaskets at surfaces whereat the top and bottom parts 200, 202 mutually abut.

Figure 4:
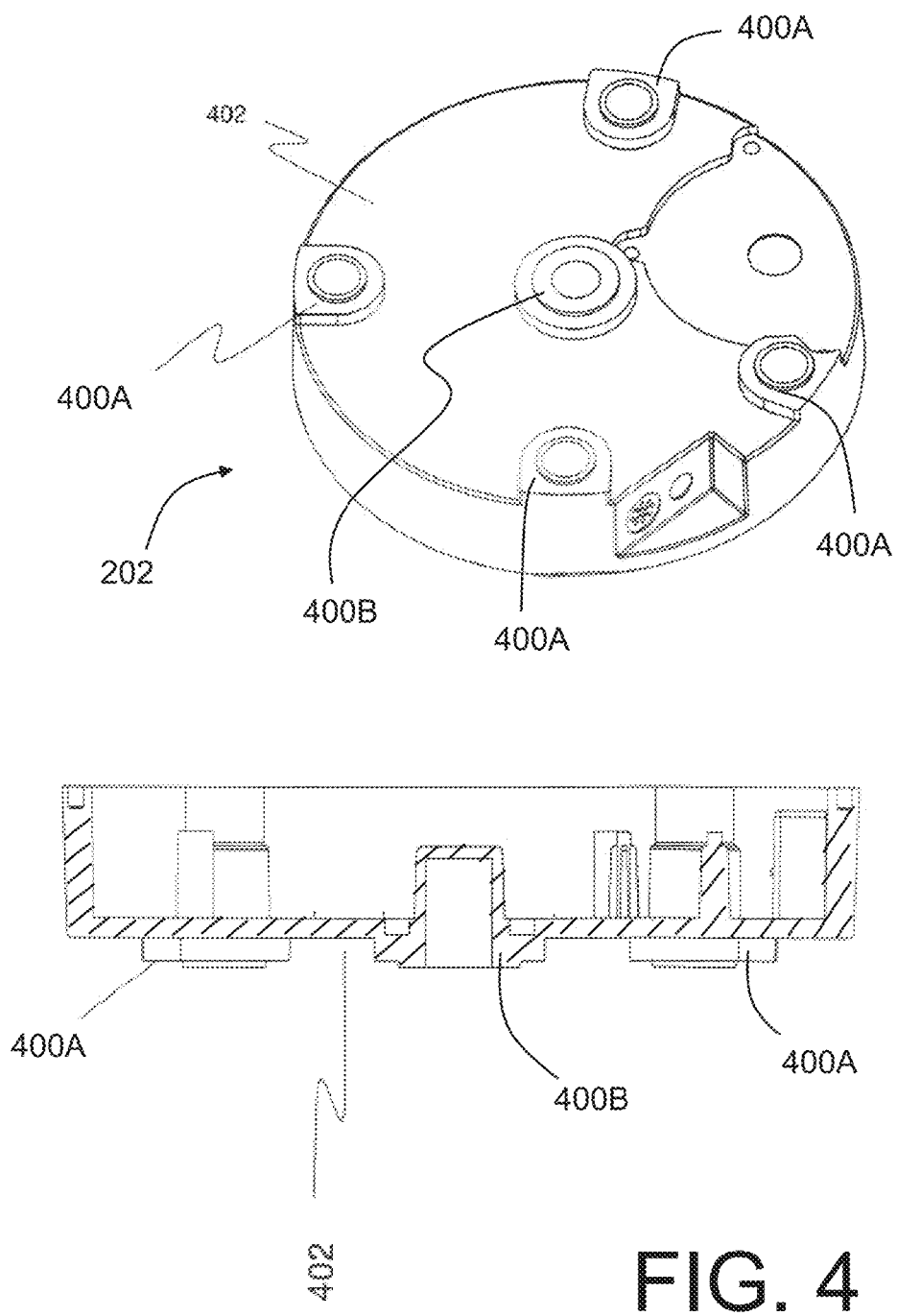
FIG. 4 is an illustration of a bottom part of the sensor device of FIG. 2, wherein the bottom part is couplable to the top part of FIG. 3 to form an external housing for the sensor device.
Figure 5:
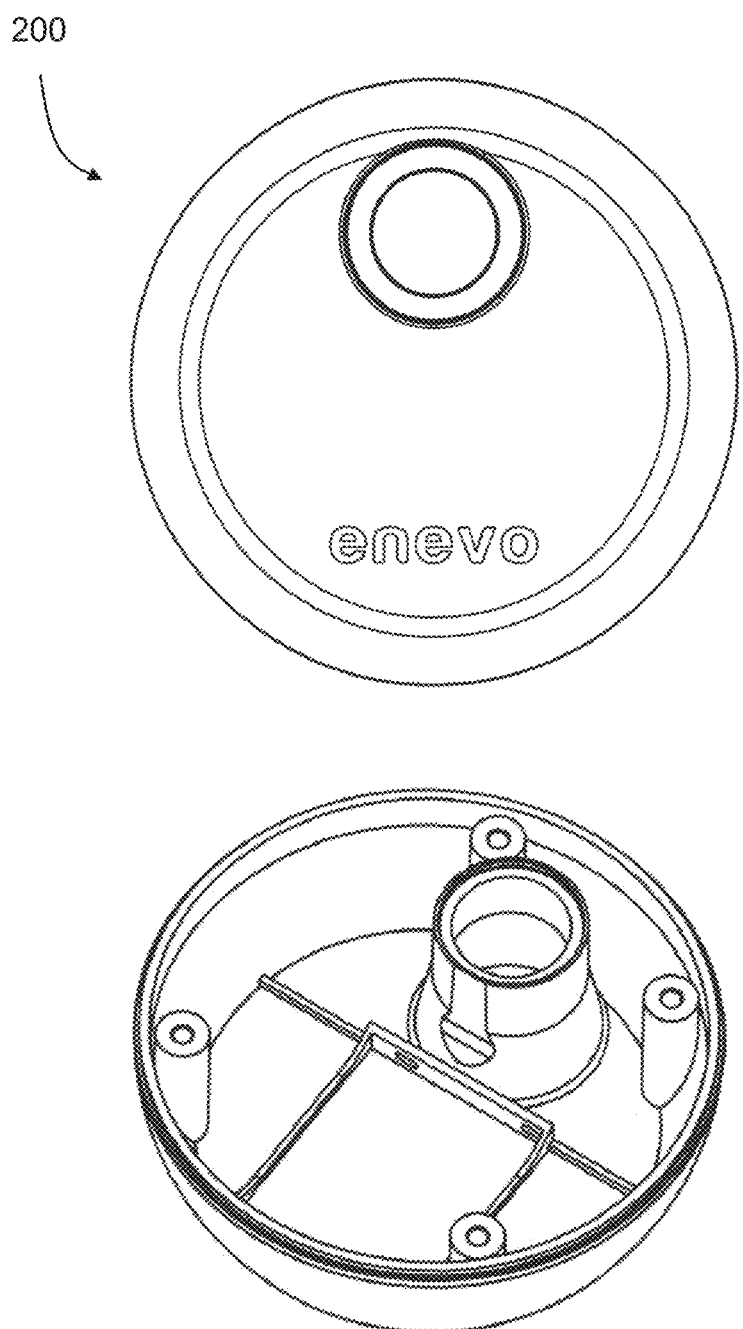
FIG. 5 is an illustration of an external appearance of the top part of FIG. 3, for example in a manner that enables registered design protection to be sought.
Figure 6:
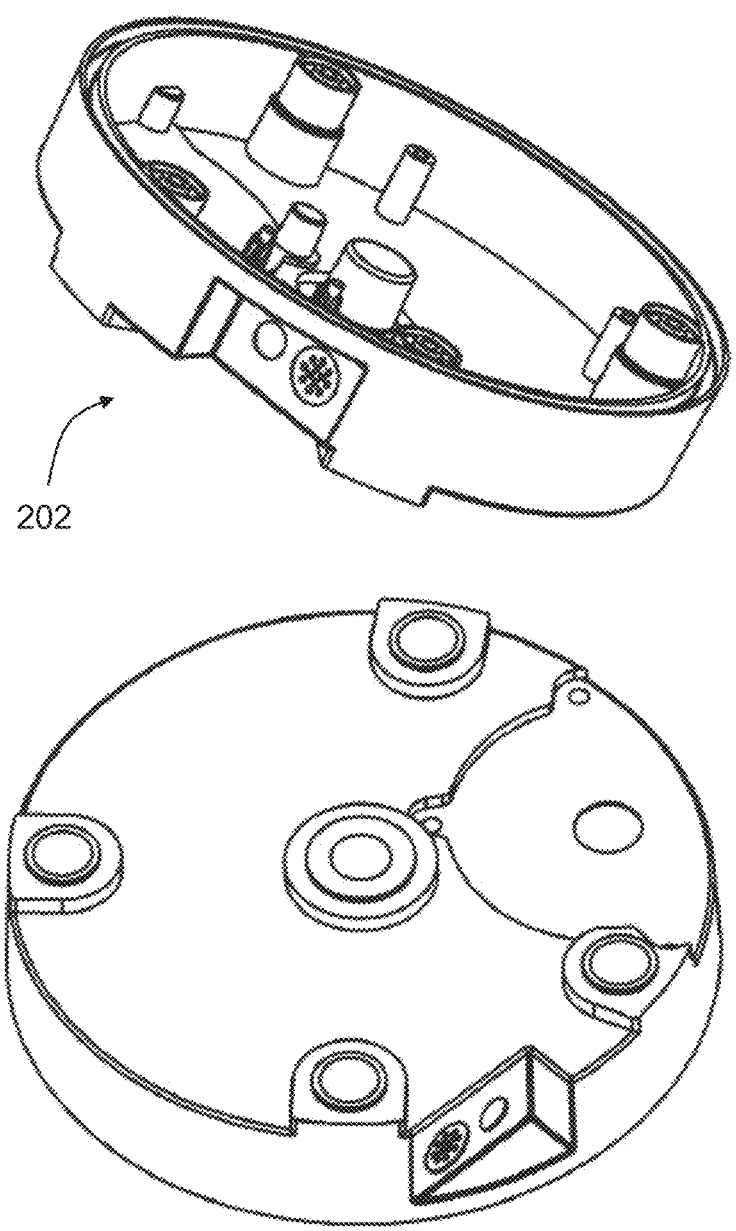
FIG. 6 is an illustration of an external appearance of the bottom part of FIG. 4, for example in a manner that enables registered design protection to be sought.

Referring next to FIG. 4, there is shown an illustration of the bottom part 202 in perspective view as seen from an underside surface 402 of the bottom part 202 which is facing towards the lid 20 of the waste container 10 when the sensor device is mounted upon the lid 20 by way of the screws 210. Four peripheral projections, namely "towers" or "spacers", denoted by 400A, are included as an integral part of the bottom part 202 for providing the aforesaid air gap 60; optionally, a central projection 400B, as illustrated, is also provided. The projections 400A present a surface area to the lid 20, when the sensor device 40 is mounted thereupon, which is small relative to area of the underside surface 402, for example less than 25% thereof, and more optionally less than 10% thereof. A peripheral recess is provided on the bottom part 202 for making connections to the sensor device 40, for example for performing field testing and diagnostics for example. Beneficially, the bottom part 202 has a peripheral diameter which is substantially constant along a height of the bottom part 202 as illustrated. The underside surface 402 beneficially has a recess, requiring one of the peripheral projections 400A to be slightly angularly displaced relative to its otherwise regular 900 position, as illustrated. The central projection 400B is beneficially provided with a blind hole as illustrated in the cross-section view of the bottom part 202; optionally, the blind hole is threaded. As aforementioned, the underside surface 402 beneficially has a white finish, for example a painted white finish, or is provided with a metallic-foil reflector, for example an Aluminium-foil reflector, for reflecting heat back towards the lid 20 when the sensor device 40 is in operation. For design registration purposes, further detailed diagrams are provided in FIG. 5 and FIG. 6 for the top part 200 and the bottom part 202 respectively.

Figure 7:
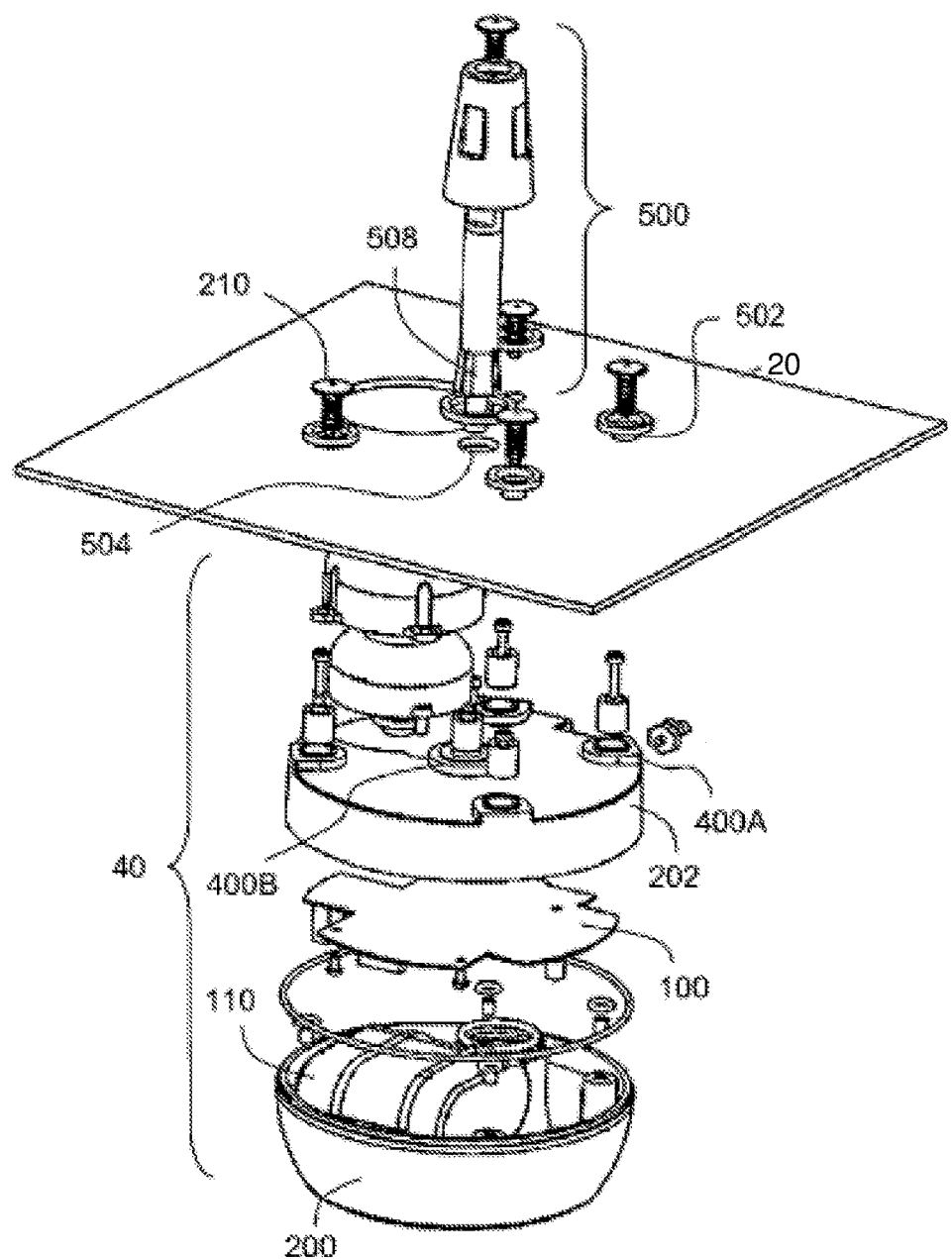
FIG. 7 is an exploded view of a tool for installing the sensor device of FIG. 2, as well as an exploded view of component parts of the sensor device of FIG. 2.

In FIG. 7, there is shown an exploded view of the sensor device 40, together with a manner in which the sensor device 40 is mounted to the lid 20 of the container 10. Moreover, there is also shown a mounting tool 500 which is operable to enable convenient installation of the sensor device 40 to the lid 20, wherein the mounting tool 500 enables a single person to execute installation of the sensor device 40 to the lid 20, even when the lid 20 is of inconveniently large size relative to an arm's reach of the person, thereby reducing a cost and time required to retrofit, for example, the sensor device 40 to pre-existing waste containers 10.

Figure 8:
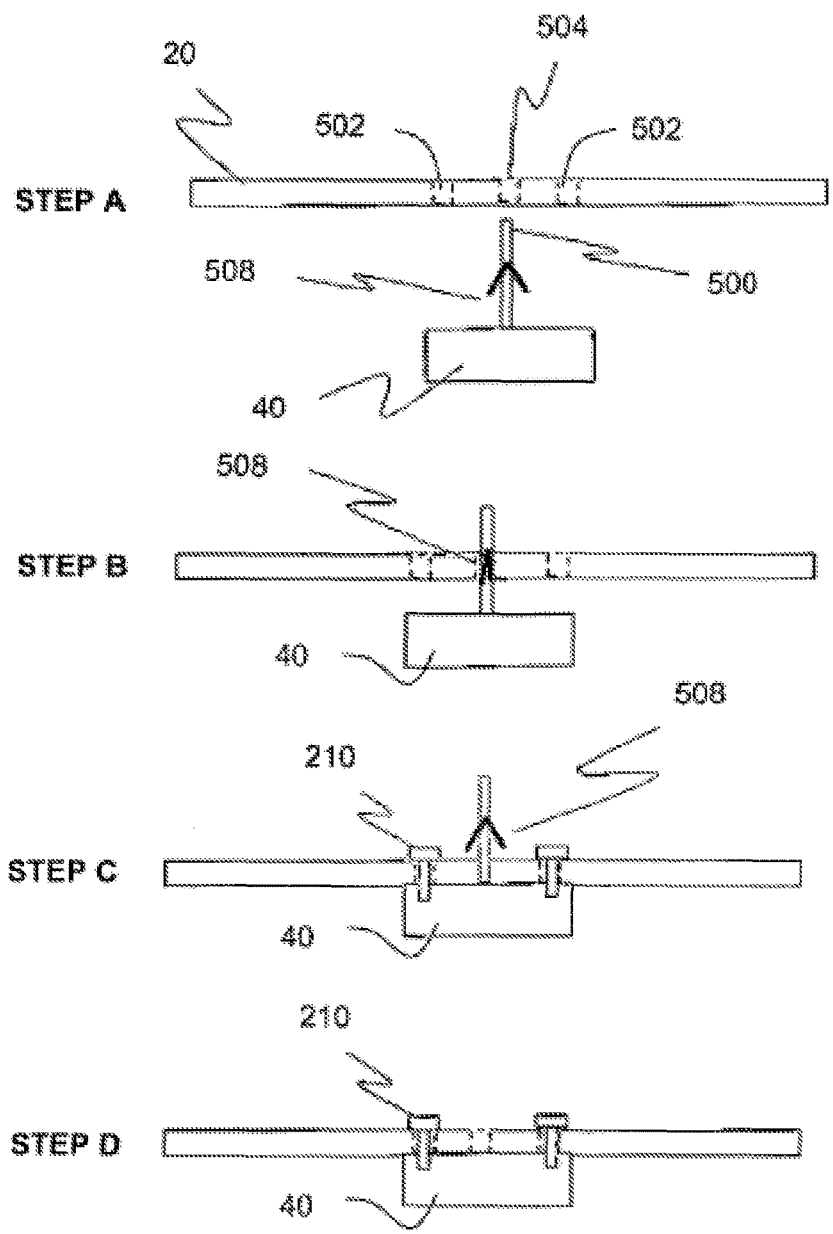
FIG. 8 is an illustration of steps of a method of installing a sensor device of FIG. 2 to a waste container for implementing a smart waste container of FIG. 1.

A practical problem encountered when implementing an automated waste management system relates to the installation and mechanical durability of the sensor device 40 to the waste container 10, either during initial manufacturing of smart waste containers 10, so-called original equipment manufacture (OEM), or retrofitting the sensor device 40 to existing non-smart waste containers. In FIG. 8, steps A to D of a method of installing the sensor device 40 to a lid 20 of a non-smart container are illustrated in a schematic manner.

In the step A, a configuration of holes is drilled into the lid 20 for later receiving the mounting tool 500 and also four screws 210. The configuration of holes is beneficially implemented by drilling, using a robust metal drilling template, to guide relative positions of the holes in the lid 20. Optionally, the configuration of holes is pre-molded into the lid 20, for example in a situation of OEM manufacture of smart waste containers. The configuration of holes includes peripheral holes 502 which align to the peripheral projections 400A for receiving the screws 210, and a central hole 504 which aligns with the central projection 400B when the peripheral holes 502 are aligned to the peripheral projections 400A. A first end of the mounting tool 500 is threaded and can be engaged into the blind hole of the central projection 400B of the bottom part 202, for example by way of a corresponding screw-thread formed into the blind hole as aforementioned. The mounting tool 500 includes a plurality of flexible wings 508 disposed approximately mid-way along an elongate length of the mounting tool 500. Beneficially, the wings 508 are fabricated from a flexible spring-like material or are rigid elements that are compliantly pivotally mounted at their proximate ends, for example the wings 508 return automatically to retracted position when mutually pressed together, but naturally assumed an outwardly splayed configuration. Thus, in the step A, a person installing the sensor device 40 drills the configuration of holes in the lid 20, if not already provided. Thereafter, the person attaches the first end of the tool 500 to the blind hole of the central projection 400B and then forces a second end of the tool 500 through the central hole 504. The wings 508 are inwardly displaced as they are forced through the central hole 504, and then assume a splayed configuration when they arrive at an opposite side of the lid 20 relative to the sensor device 40.

In the step B, the person forces the mounting tool 500 so that the wings 508, in retracted position, are also forced through the central hole 504 as illustrated.

In the step C, the person forces the mounting tool 500 a sufficient distance through the central hole 504 such that the wings 508 become splayed out on an opposite side of the lid 20 to that which the sensor device 40 is facing. Thereafter, with the tool 500 retaining the sensor device 40 held to the lid 20, the person applies the four screws 210 through the peripheral holes 502 to engage into holes corresponding to the peripheral projections 400A and then tightens the screws 210. The screws 210 thereby hold the sensor device 40 firmly to the lid 20.

The screws 210 used for the fastening can be of a variety of designs and have an associated functionality to prevent any unauthorised removal of the sensor device 40. Optionally, the screws 210 have threads, hooks, cone shaped surfaces, wedges, or also be integrated in the sensor device 40 or the lid 20 as required.

In the step D, the person removes the mounting tool 500 from the sensor device 40 to complete the installation of the sensor device 40.

Figure 9:
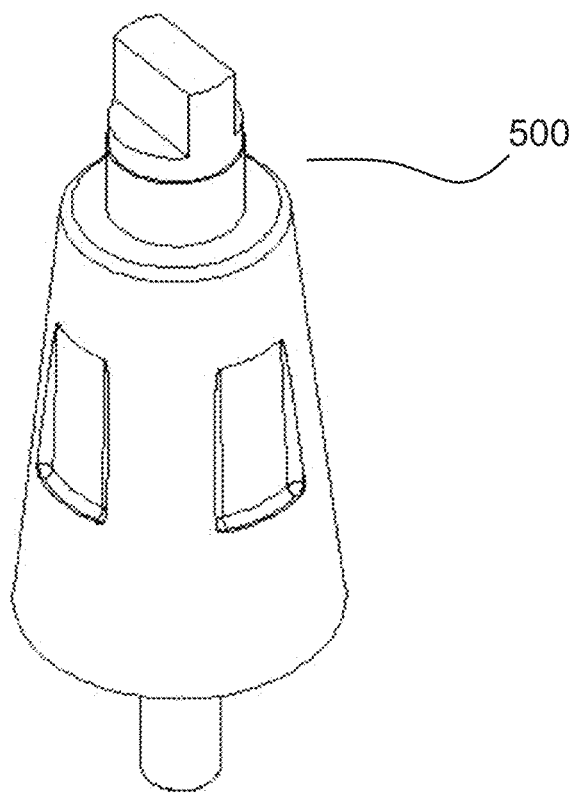
FIG. 9 is a view of a portion of the mounting tool of FIG. 7 which is used for attaching a sensor device of FIG. 2 to a lid of a waste container of FIG. 1.

In FIG. 9, there is shown a view of a portion of the mounting tool 500 which is used for attaching the sensor device 40 to the lid 20.

Figure 10:
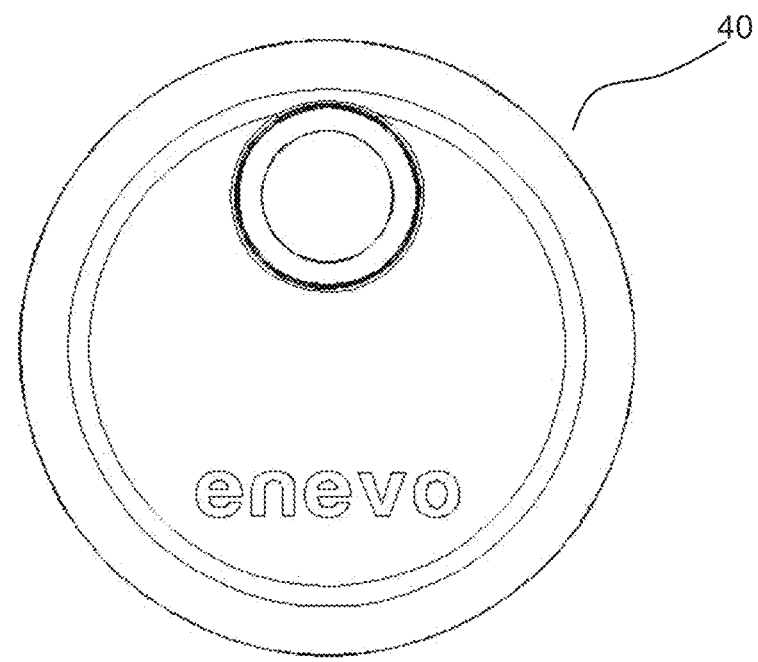
FIG. 10 are illustrations of different views of the sensor device in FIG. 2.
Figure 10:
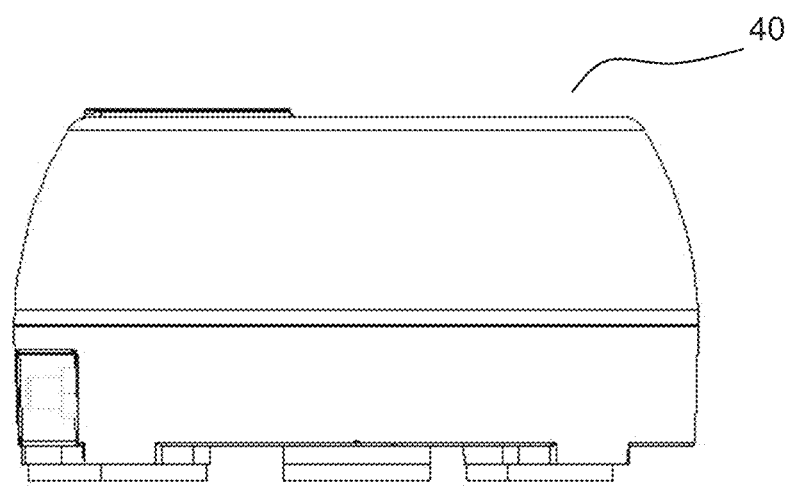
Figure 10:
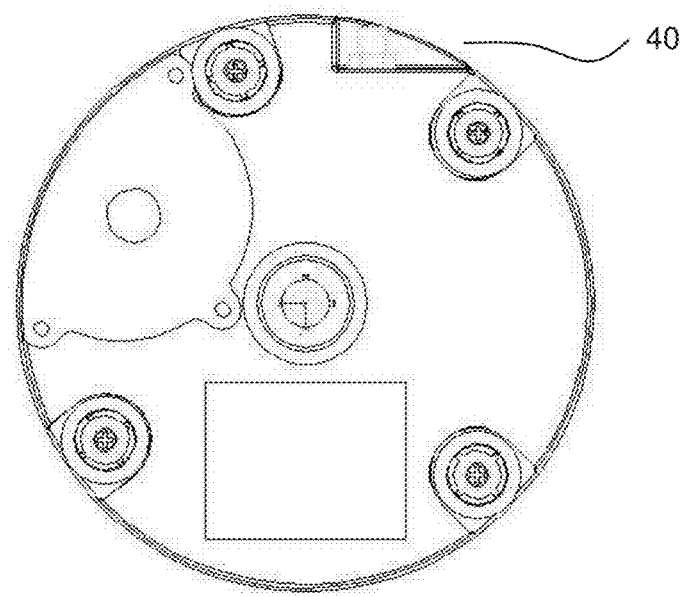
Figure 10:
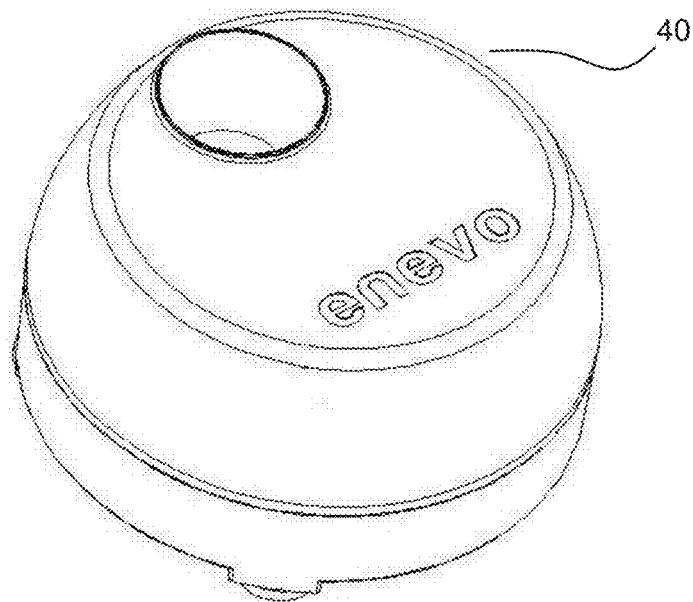

In FIG. 10, there are shown different views of the sensor device 40 including:
FIG. 10(*a*) a front view;
FIG. 10(*b*) a side view;
FIG. 10(*c*) a bottom view; and
FIG. 10(*d*) a perspective view.

In the foregoing, installation of the sensor device 40 to the lid 20 of the container 10 is described. It will be appreciated that the sensor device 40 is beneficially mounted at an upper portion of the main body 30. An alternative mounting position for the sensor device 40 is on one or more inside surfaces of side-walls of the main body 30, preferably where the sensor device 40 will not be in contact with the waste 80 when the container 10 is tipped in operation to remove the waste 80 during waste collection activities.

It will be appreciated that the sensor device 40 is optionally manufactured as a two-part arrangement, namely an active unit and a support holster which is attached to the lid 20 as aforementioned, or inside-surface side walls at an upper portion of the main body 30. The holster is operable to retain the active unit in a secure manner, for example via a locking arrangement, such that the active unit can be detached, for example by authorized personnel, in an event that the active unit needs to be serviced or replaced.

In an alternative embodiment, the sensor device 40 is optionally installed in or attached to the walls of the waste container 10 or to any other suitable part of the waste container 10. For example, the waste container 10 optionally has a top part with only a small opening with a lid 20. In this embodiment, it is optionally beneficial to install the sensor device 40 in the top part, known as a "roof" or "celling", of the waste container 10. Moreover, the waste container 10 optionally has a lid 20 or an opening in one or more sides of the waste container 10. In such an embodiment, it is optionally beneficial to install the sensor device 40 to another part of the waster container 10 other than the lid 20, for example to the top part or back wall or side walls of the waster container 10.

Modifications to aspects of the disclosed embodiments described in the foregoing are possible without departing from the scope of the disclosed embodiments as defined by the accompanying claims. Expressions such as "including", "comprising", "incorporating", "consisting of", "have", "is" used to describe and claim the present disclosed embodiments are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A sensor system comprising a sensor device (40) for remote monitoring of a waste container (10), the sensor device (40) comprising:
   one or more sensors (70) for sensing an amount of waste (80) and an environment within the waste container (10);
   a data processing unit (100) for processing sensor signals generated by the one or more sensors (70) indicative of the amount of waste (80) in the waste container (10) and the environment within the waste container (10);
   a communication interface (90) coupled to the data processing unit (100) for enabling the sensor device (40) to communicate information corresponding to the sensor signals to a remote location relative to the sensor device (40);
   a powering unit (110) to power up the sensor device (40);
   wherein the sensor system further comprises one or more spacing elements (50), a heat reflecting layer and a mounting arrangement for mounting the sensor device (40) to an underside surface of an upper lid (20) of the waste container (10) in a spaced apart manner by placing the one or more spacing elements (50) in combination with the heat reflecting layer arranged between the sensor device (40) and the upper lid (20) of the waste container (10) so as to provide a thermal barrier between an underside surface of the waste container lid (20) and an external surface of the sensor device (40); and
   wherein the heat reflective layer arranged between the sensor device (40) and the upper lid (20) of the waste container (10) is a reflective metal foil to enable the sensor device (40) to maintain a workable operating temperature.

2. The sensor system as claimed in claim 1, wherein the one or more spacing elements (50) in combination with an air gap (60) is adapted to maintain the sensor device (40) at an acceptable temperature during operation.

3. A sensor system as claimed in claim 1, wherein the thermal barrier (60) includes the air gap between a majority of the area (402) of the sensor device (40) and the upper portion (20) of the waste container (10).

4. A sensor system as claimed in claim 1, wherein the thermal barrier (60) has a height in a range of 1 mm to 20 mm, when the sensor device (40) is mounted in operation to the upper portion of the [waste container (10).

5. A sensor system as claimed in claim 1, wherein the thermal barrier (60) has a height in a range of 2 mm to 10 mm, when the sensor device (40) is mounted in operation to the upper portion of the waste container (10).

6. A sensor system as claimed in claim 1, wherein the thermal barrier (60) includes the reflective metal foil for reflecting thermal radiation from the upper portion of the waste container (10) back towards the upper portion.

7. A sensor system as claimed in claim 1, wherein the sensor device (40) is arranged to be attachable to the upper lid (20) of the waste container (10) through the mounting arrangement.

8. A sensor system as claimed in claim 1, wherein the sensor device (40) is filled with a filler material in order to provide mechanical stability for the sensor device (40).

9. The sensor system as claimed in claim 1, wherein the one or more sensors comprises one or more of:
   (a) a sensor for determining the quantity of waste (80) present within the waste container (10);
   (b) a temperature sensor for measuring a temperature within the waste container (10);
   (c) a gas sensor for monitoring atmospheric conditions within the waste container (10); and
   (d) a humidity sensor for measuring humidity within the waste container (10).

10. A sensor system as claimed in claim 9, wherein the sensor for determining the quantity of waste (80) present within the waste container (10) is implemented by way of an ultrasonic sensor arrangement (300).

11. A sensor system as claimed in claim 10, wherein the ultrasonic sensor arrangement (300) is included within a housing (200, 202) of the sensor device (40) and has a port (300), wherein the ultrasonic radiation is emitted and received in operation, disposed inside an outwardly-tapered hole (206) implemented through the housing (200, 202) through which condensation is ducted in operation.

12. A sensor system as claimed in claim 9, wherein the gas sensor for monitoring atmospheric conditions within the waste container (10) is implemented by way of a hydrocarbon gas sensor.

13. A sensor system as claimed in claim 11, wherein the ultrasonic arrangement is included within a housing (200, 202) of the sensor device (40) and has a port (300), whereat ultrasonic radiation is emitted and received in operation, disposed inside an outwardly-tapered hole (206) implemented through the housing (200, 202) through which condensation is ducted in operation.

14. A sensor system as claimed in claim 1, wherein the sensor device (40) comprises one or more peripheral projections (400A) for defining the thermal barrier (60) when the sensor device (40) is mounted to the waste container (10).

15. A sensor system as claimed in claim 1, wherein the sensor device (40) comprises a coupling arrangement (400B) for receiving a tool (500) for use in retaining the sensor device (40) to the waste container (10) for enabling one or more fasteners (210) to be installed to attach the sensor device (40) to the waste container (10).

16. A sensor system as claimed in claim 1, wherein the ultrasonic sensor arrangement (300) is included within a housing (200, 202) of the sensor device (40) and the inside of the housing (200, 202) is filled with a filler material with lower density than the material of the housing of the sensor device (40).

17. The sensor system as claimed in claim 1, wherein the data processing unit (100) is configured for transmitting information corresponding to one or more sensor signals in a constant manner or in a periodic manner to a remote monitoring station when the one or more sensor signals exceed a predefined threshold value.

18. A sensor system as claimed in claim 8, wherein the filler material is polyurethane foam.

19. A sensor system comprising a sensor device (40) for remote monitoring of a waste container (10), the sensor device (40) comprising:
- one or more sensors (70) for sensing an amount of waste (80) and an environment within the waste container (10);
- a data processing unit (100) for processing sensor signals generated by the one or more sensors (70) indicative of the amount of waste (80) in the waste container (10) and the environment within the waste container (10);
- a communication interface (90) coupled to the data processing unit (100) for enabling the sensor device (40) to communicate information corresponding to the sensor signals to a remote location relative to the sensor device (40);
- a powering unit (110) to power up the sensor device (40);
- wherein the sensor system further comprises one or more spacing elements (50), a heat reflecting layer and a mounting arrangement for mounting the sensor device (40) to an underside surface of an upper lid (20) of the waste container (10) in a spaced apart manner by placing the one or more spacing elements (50) in combination with the heat reflecting layer arranged between the sensor device (40) and the upper lid (20) of the waste container (10) so as to provide a thermal barrier between an underside surface of the waste container lid (20) and an external surface of the sensor device (40); and
- wherein the thermal barrier includes a reflective metal foil for reflecting thermal radiation from the upper portion of the waste container (10) back towards the upper portion.

20. The sensor system according to claim 19 wherein the heat reflective layer arranged between the sensor device (40) and the upper lid (20) of the waste container (10) is a reflective metal foil to enable the sensor device (40) to maintain a workable operating temperature.

* * * * *